United States Patent [19]

Nelson et al.

[11] Patent Number: 4,736,103

[45] Date of Patent: Apr. 5, 1988

[54] SPECTROMETER TEST GAS CHAMBER

[75] Inventors: Robert L. Nelson; William J. Danley; William H. McIntyre, all of Orrville, Ohio

[73] Assignee: Westinghouse Electric Corp., Pittsburgh, Pa.

[21] Appl. No.: 837,439

[22] Filed: Mar. 7, 1986

[51] Int. Cl.$^4$ .................... G01N 21/35; G02F 1/11
[52] U.S. Cl. .................... 250/343; 250/339; 250/353
[58] Field of Search ............ 250/343, 373, 353, 339; 356/437, 410

[56] References Cited

U.S. PATENT DOCUMENTS

| | | | |
|---|---|---|---|
| 3,281,597 | 10/1966 | Greenburg | 250/343 |
| 3,699,339 | 10/1972 | Taczak, Jr. | 250/353 |
| 3,751,664 | 8/1973 | Falbel | 250/353 |
| 4,205,913 | 6/1980 | Ehrfeld et al. | 250/343 |
| 4,276,475 | 6/1981 | Nelson | 250/373 |

FOREIGN PATENT DOCUMENTS 813205  3/1981  U.S.S.R. ............ 250/343

Primary Examiner—Carolyn E. Fields
Attorney, Agent, or Firm—E. C. Arenz

[57] ABSTRACT

A detector assembly of a spectrometer device which includes a built-in test gas chamber, has a housing defining a chamber with a first end having a first aperture and a second end having a second aperture opposite the first aperture. While light transmissive windows can be mounted in the opposed apertures to enclose the chamber, it is preferred that a focusing lens be mounted in the first aperture and a detector in the second aperture in order to enclose the housing ends and define the chamber. The chamber has a cone-like inner surface tapering from the first aperture to the second aperture. The housing has a test gas inlet in communication with the chamber and disposed proximate the first end thereof. A test gas outlet is in communication with the chamber and disposed proximate the second end. The test gas inlet is so oriented as to introduce test gas into the chamber on a tangent to the first end, first aperture resulting in a tangential flow path direction within the cone-like chamber.

5 Claims, 3 Drawing Sheets

SPECTROMETER TEST GAS CHAMBER

BACKGROUND OF THE INVENTION

1. Field of the Invention

The present invention relates to gas analyzers. In particular, the present invention provides an improved test gas chamber for use with conventional spectrometers as well as automated acousto-optic infrared analyzer systems in which test gases are used for the calibration of such devices.

2. Description of the Prior Art

Conventional on-line in-situ gas spectrometers measure a limited number of gases. These devices are of the NDIR type which use a broad band of light that is centered at the absorption peak of the gas molecule of the species of interest. This broad band is easily selected from all the light frequencies emitted by the source through the use of a passband filter. In order to calibrate such devices, cells which are constructed from light-transmitting materials and which contain a sample of the specific gas of interest are inserted into the path of the light beam in order to calibrate the instrument. When the instrument measures more than one gas, several individual sealed gas cells are selectively inserted into the path of the beam. The up-scale readings given by these known cells can then be extrapolated to a zero value for calibration purposes.

A large and growing market exists for analytical devices which can be used to analyze the reaction products of a wide variety of industrial processes. In addition, on-line real time combustion product analyzers are needed to facilitate the more efficient burning of hydrocarbon fuel. For example, the electric utility industry has been faced with the task of monitoring stack emissions for some years. At first, the monitored emissions consisted of measuring the oxygen concentration and of monitoring smoke opacity in order to control combustion efficiency. Continued increases in the number of regulations have lead to the necessity of monitoring sulfur oxides and nitrogen oxides. Additional constituents will undoubtedly also require monitoring in the future. Proposed regulations in Europe, for example, will require the monitoring of ammonia if it is added to the stack to maintain precipitron efficiency. Recent studies have shown that increased combustion efficiency can be achieved if carbon monoxide is monitored. Therefore, the list of gases which are of interest to commercial activities has rapidly grown to larger and larger numbers. The historical solution has been to installed a separate sensor to monitor each gas. This approach becomes more and more expensive and a less desirable approach as the total number of gases for which monitoring is required increases.

It is known to employ analytical devices which utilize ultraviolet and infrared spectrophotometry, as well as gas and liquid chromatography in order to meet the industrial needs discussed above. Such optical instruments utilize the following important characteristics of the materials being analyzed. A particular molecule has a characteristic absorption spectrum which is dissimilar to that of all other molecules. The spectra of mixtures of molecules are additive and the absorption is proportional to the concentrations of the molecules. Optical absorption spectra can be obtained from any type of sample be it solid, liquid or gas so long as the sample is optically transmissive, and the spectra can be obtained in a non-destructive testing of the sample. Almost all gas molecules absorb infrared radiation. Each molecule has its absorption at specific characteristic wavelengths, so that by monitoring the magnitude of the absorption at the specific wavelengths, the amount of gas present in the stack may be deduced. This is accomplished by transmitting infrared radiation across the stack to a detector. The wavelength of the transmitted radiation is tuned to coincide with the specific wavelength of the gas to be measured. The strength of the detector signal at a given wavelength correlates with the concentration of the absorbing gas at that wavelength. The selective tuning of the infrared radiation is accomplished either by inserting narrow band interference filters in the path, or by inserting cells containing appropriate gas fills in the path. Both of these approaches involve mechanical motion, and the number of cells or filters that can be employed is obviously limited. Thus, reliability and accuracy suffer from the less than ideal properties of these tuning elements.

It has recently been recognized that certain birefringent optical materials which are termed acousto-optic materials can be used as a filter in a spectrum analyzer. U.S. Pat. No. 3,792,287 which is assigned to the assignee of the present invention and incorporated herein by reference teaches the use of an efficient infrared transmissive acousto-optic material, thallium-arsenic-selenide which offers the possibility of operation over the near to mid-infrared spectrum from about 1 micrometer to about 16 micrometers. An automated acousto-optic infrared analyzer system which utilizes acousto-optic technology is described in U.S. Pat. No. 4,490,845 which is assigned to the assignee of the present invention and incorporated herein by reference. This patent teaches an automated acousto-optic tunable filter infrared analyzer system which permits rapid electronic tuning of the filter to a selected infrared bandpass via the acousto-optic interaction with infrared radiation which has passed through a sample. The infrared analyzer system includes means for detecting infrared radiation through the sample to be analyzed, which sample has a predetermined infrared absorption characteristic. Means are provided for directing the infrared radiation through an acousto-optic tunable filter. An acousto-optic tunable filter includes an optically aligned acousto-optic crystal through which infrared radiation is passed at a predetermined angle relative to the crystal optic axis. An acoustic transducer is coupled to the crystal and a variable frequency RF energy source whereby acoustic waves are launched in the crystal in order to interact with the selected narrow bandwidth portion of the polarized infrared radiation to make it distinguishable from the remaining radiation. The tuned or selected narrow bandwidth radiation is a function of the frequency of the RF energy source which is connected to the acoustic transducer of the filter. Infrared radiation detection means are coupled to the filter in order to detect the output filtered infrared radiation and to generate an output signal as a function of the output filtered infrared radiation. Automated computing means are provided with the detection means output electrical signal. The computing means includes means for selectively activating the RF energy source to determine the timing and frequency of RF energy applied to the acoustic transducer to thereby determine the selected or filtered narrow bandwidth infrared wavelength of interest.

A specific application of an acousto-optic infrared analyzer system for monitoring stack gas emissions is disclosed in U.S. patent application Ser. No. 736,199, filed May 20, 1985, now U.S. Pat. No. 4,652,756, and assigned to the assignee of the present invention. In such an acousto-optic tunable filter based spectrometer, a large number of different gases can be measured. In order to establish the correct operating parameters of the system as well as to calibrate the system, test gas requirements could involve a wide range of gases and concentrations. Obviously, it becomes quite costly and very impractical to build a large number of test gas cells either into the device or to provide them for use with the device as is the present practice with on-line gas spectrometers. Additionally, the added cost of the light transmitting windows used to contain test gases for the infrared wavelengths is not desirable.

It is therefore an object of the present invention to provide an improvement to the detector assembly of a spectrometer consisting of a focusing lens and a sealed detector. The addition of a housing designed to mate and seal to the focusing lens and the detector housing or detector window defines a test gas chamber formed between these two light-transmitting elements whereby test gases can be selectively introduced into and removed from this test gas chamber.

It is also an object of this invention to provide a test gas chamber in which the focusing lens serves as the only barrier between the detector means and the process or sample gas being analyzed.

It is a further object of this invention to provide an improvement to an automated acousto-optic infrared analyzer system which improvement consists of an integral test gas chamber.

It remains another object of this invention to provide a test gas chamber design which minimizes the chamber volume and still facilitates the unimpeded focus of the beam onto a detector means.

It is still an object of this invention to provide a test gas chamber with a unique method of test gas introduction whereby a tangential flowpath direction within the gas chamber is established.

SUMMARY OF THE INVENTION

The invention provides for the design of a detector assembly used with a spectrometer device to include a built-in test gas chamber. A test gas chamber means includes a housing defining a chamber with a first end having a first aperture of a first dimension and a second end having a second aperture of a second lesser dimension opposite the first aperture. The chamber has a cone-like inner surface tapering from the first aperture to the second aperture. The housing means has a test gas inlet means in communication with the chamber and disposed proximate the first end thereof. A test gas outlet means is in communication with the chamber and disposed proximate said second end. The test gas inlet means is so oriented as to introduce the test gas into the chamber on a tangent to the first end first aperture. As a result, a tangential flow path direction is achieved within the cone-like chamber. The cone-like dimension of the chamber reduces the volume of the test gas chamber and thus the amount of test gas required.

In a preferred embodiment, the invention provides an improvement to a spectrometer device of the type which includes a focusing lens means for directing light onto a detector means. The improvement comprises an integral test gas means defining a chamber therewithin disposed between and including as integral members thereof the focusing lens means disposed at a first end and the sealed detector means disposed at the second end. In this configuration, no additional cost is incurred in the supply of additional windows or lenses. The focusing lens on the detector side of the process can serve as a lens as well as a barrier to the leakage of process gas. In addition, the infrared window mounted as an integral part of the detector can serve as a second barrier since the detector as manufactured is under a vacuum and is hermetically sealed. As a result, by utilizing a chamber with O-ring seals that mate with the cylindrical housing of the detector and with the focusing lens, a chamber is provided for use with test gas that does not require any additional IR windows.

The test gas chamber is purged or flooded with the test gas of interest by admitting test gas into the chamber at a first location and venting that gas from the test chamber at a second location. The time required for this flooding or purging operation as well as the volume of gas needed to achieve the same is reduced because the test gas chamber volume is minimized by shaping it to match the cone of light focused by the lens on the detector. By admitting the test gas on a tangent to the large diameter end and extracting the gas at the small end of the chamber, the flooding and purging operation of the detector chamber is facilitated.

BRIEF DESCRIPTION OF THE DRAWINGS

The above as well as other features and advantages of the present invention can be readily appreciated through consideration of the detailed description of the preferred embodiment in conjunction with the several drawings in which.

DESCRIPTION OF THE PREFERRED EMBODIMENT

Figure 1:
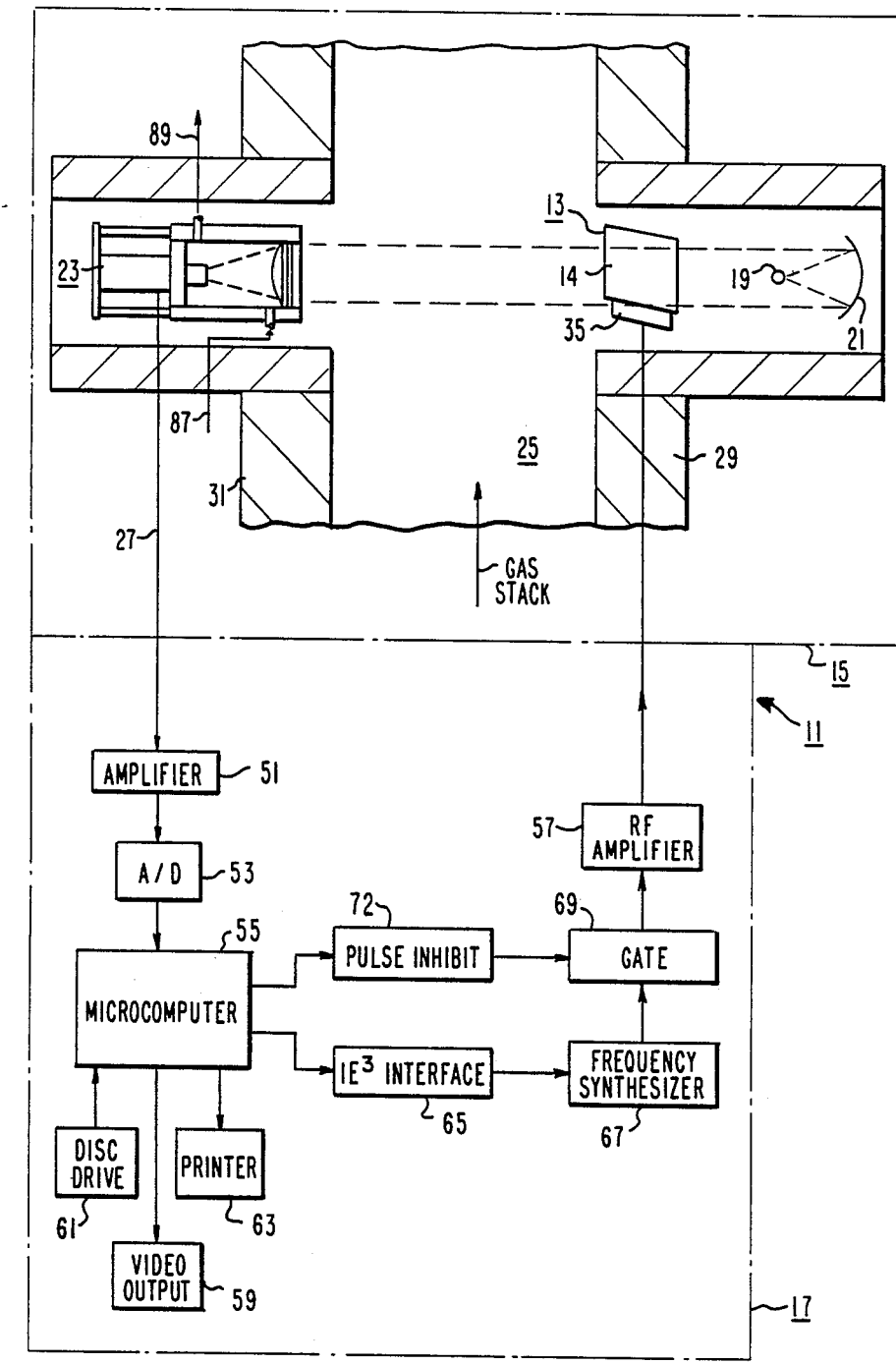
FIG. 1 is a schematic illustration of an embodiment of an improved acousto-optic infrared analyzer system with test gas chamber all according to the present invention therein.

The improved spectrometer test gas chamber of this invention is ideally suited for use in an automated acousto-optic tunable filter infrared analyzer system. Such a system is schematically represented in FIG. 1 and is generally indicated by the reference character 11. The acousto-optic tunable filter infrared analyzer system (AOTF) 11 is configured from several subsystems and components including an acousto-optic tunable filter 13. The analyzer system 11 can be viewed as having two major subsystems, an optical subsystem 15 and an electronic subsystem 17. The optical system 15 of the analyzer system 11 is essentially an infrared solid state spectrometer which has been designed to permit operation over a relatively wide spectral range. An infrared radiation source 19, such as a Nernst glower, is used as the primary source of broadband infrared radiation for the system. A portion of the output infrared radiation from the source 19 is collected and collimated by a mirror 21.

The collimated beam from the mirror 21 is passed through the AOTF 13 in which a narrow bandwidth portion of the radiation is selected and distinguished from the remaining infrared radiation as shown by the dash-lines of FIG. 1. A detector means 23 is aligned so as to collect the spatially separated narrow band interacted radiation output from the AOTF 13 after it passes through an environment of interest generally indicated at 25 such as, for example, an industrial process stack. The detector means 23 will be described below in detail in conjunction with FIGS. 2, 3A, 3B and 3C. The detector means 23 provides an output as at 27 for processing in a manner to be described below. The environment of interest in the particular application illustrated herein is a gas stack of, for example, an industrial processing plant or a utility, and is generally indicated by the reference character 25. As can be seen from the schematic illustration of FIG. 1, the gas stack 25 includes opposed side walls 29 and 31. In this configuration, the detector means 23 and the source means containing the AOTF 13 are placed on opposite sides of the stack 25. By separating the detector and the AOTF, the angular displacement of the narrow band interacted radiation is adequate to separate it spatially from the broad-band non-interacted radiation at the detector. This process generally described above can be studied in detail through reference to U.S. Pat. Nos. 4,490,845 and 4,652,756, which are assigned to the assignee of the present invention and which are incorporated herein by reference. Additionally, U.S. Pat. No. 4,505,550 to Steinbruegge which is assigned to the assignee of the present invention and incorporated herein by reference, teaches the use of input and output polarizers for an AOTF.

The acousto-optic tunable filter 13 operates through the interaction of acoustic waves with light in a suitable crystal 14. Typically, an acoustic transducer 35 is bonded to the optical crystal 14 and is driven by a controlled RF signal as will be described hereinafter. Various optical materials have been developed for use in acousto-optic devices. These materials include thallium-arsenic-selenide as described in U.S. Pat. No. 3,792,287, thallium-phosphorus-selenide per U.S. Pat. No. 3,929,970 and thallium-arsenic-sulfide per U.S. Pat. No. 3,799,659, all of which patents are assigned to the assignee of the present invention and incorporated herein by reference.

The electronic system 17 as illustrated in FIG. 1, will now be described. The analog output signal from the infrared detector means 23 is provided via 27 to an amplifier 51 and to an analog-to-digital converter 53 with the resultant digital signal applied to microcomputer 55. The electrical system 17 interfaces with the optical system 15 at the acousto-optic tunable filter 13 via the transducer 35 which is connected to the RF amplifier 57. Selected frequency RF drive power is applied via the transducer 35 in order to launch acoustic waves into the crystal 14. In this way, optically filtered infrared radiation can be detected and utilized by the microcomputer to determine the absorption resulting from the presence of selected gases in the gas stack 25. The microcomputer 55 typically has a video output means 59 associated therewith for visual display of detected signals, as well as memory means such as a disk drive 61 and a printer 63. The memory means 61 stores the control and operation signal for the system. The microcomputer 55 through an appropriate interface means 65, when supplied with control signals from the memory means 61, controls the output frequency and amplitude from a frequency synthesizer 67 which is connected by a gate means 69 to the RF amplifier 57 for pulsed operation. The gate 69 is utilized in conjunction with a pulse inhibit circuit means 72 in order to provide assurance that the RF pulse of the proper width is applied to the transducer while the RF power duty cycle is limited to a load level which does not overheat the crystal 14. This system is thus capable of operating not only as a rapidly tunable narrow band infrared filter but also as a solid state optical chopper.

Control signals from the memory means 61 are applied to the microcomputer 55 in order to sequentially apply RF pulses to the transducer 35 of the acousto-optic tunable filter 13. The pulses are designed to cause the filter to be transmissive at a reference wavelength where there is no absorption and then at a wavelength where a known gas has a relatively strong absorption. In addition to rapidly sampling the absorption wavelength for a variety of gases, the system is initialized with no gas present to yield the sample amplitude signal as measured by the analog-to-digital converter for the reference wavelength. The microcomputer can then be utilized to generate feedback process control signals as a function of the analysis to control the particular process, such as combustion, which is being analyzed.

Figure 2:
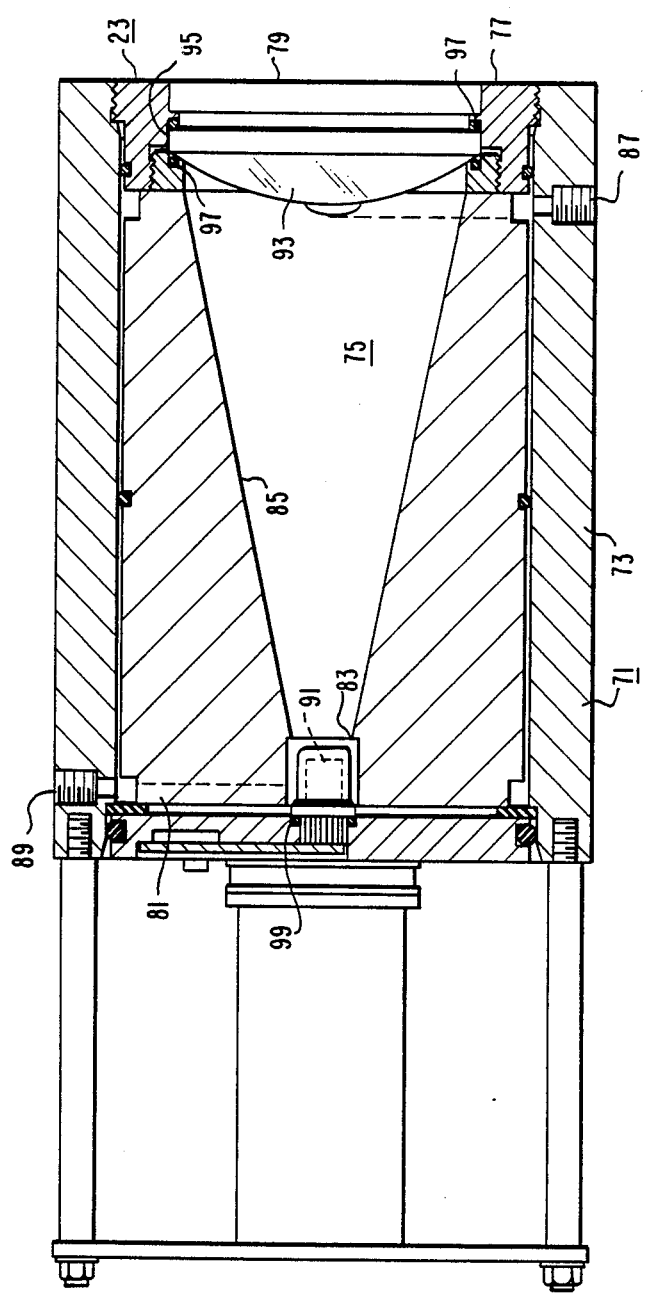
FIG. 2 is a cross-sectional representation of the test gas chamber according to this invention incorporating an integral focusing lens and detector element therein.

The detector means generally indicated by the reference character 23 in FIG. 1 is shown in detail in the cross-sectional view of FIG. 2. The detector means 23 includes a test gas means 71 defined by a housing means 73. The housing means 73 includes a chamber 75 with a first end 77 having a first aperture 79 of a first dimension. The housing means 73 further includes a second end 81 having a second aperture 83 therein. The second aperture is of a lesser dimension than the first aperture 79 of the first end 77 and is disposed at the opposite end of the housing relative to the first aperture 79. The housing 71 can be manufactured from a single member to provide an integral structure or can be manufactured from several components. The chamber 75 defines therein a cone-like inner surface or face 85 tapering from the first aperture 79 to the second aperture 83. The housing means 71 further includes a test gas inlet means 87 in communication with the cone-like chamber 75 and disposed proximate the first end 77 of the housing 71. A test gas outlet means 89 is disposed in communication with the chamber 75 and is proximate the second end 83.

In the preferred embodiment of this invention, an infrared detector 91 is disposed in the second end 83 of the housing. The detector 91 includes an infrared window mounted as an integral part of the detector and this detector window can serve as one barrier of the test gas chamber since such detectors 91 are manufactured under a vacuum and hermetically sealed. Suitable detectors are available from Infrared Industries, Eastern Division, Orlando, Fla. and Opto Electronics, Petaluma, Calif. On the opposite side of the housing means and the first aperture 79, a focusing lens 93 serves as both a lens and a barrier to the leakage of process gas into the cone-like test gas chamber 75. The lens 93 is mounted in a seat 95 in the housing and sealed therein by means of O-rings 97. Likewise, a seal is established between the detector 91 and the second aperture 83 of the housing 71 by means of at least one O-ring 99.

It should be appreciated by using the detector 91 and the focusing lens 93 as members of the test gas chamber, it is possible to eliminate the use of additional infrared windows mounted in the housing. As a result, by designing a chamber with O-ring seals that mate with the cylindrical housing of the detector and the focusing lens, one can obtain a chamber for test gas purposes that does not require any additional IR windows.

Through the inlet means 87, the test gas chamber is purged or flooded with test gas of interest by admitting test gas to the chamber via the vent 87 and venting the gas through the vent means 89. It should be appreciated that the test gas chamber 75 has a volume which is minimized by shaping it to match the cone of light focused by the lens 93 onto the detector 91. Furthermore, by admitting the test gas on a tangent to the large diameter end and extracting the gas at the small end of the chamber, the time necessary to achieve the purge is reduced.

Figure 3A:
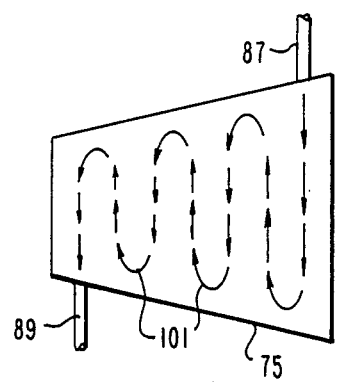
FIGS. 3A, 3B and 3C schematically represent the test gas flowpath within the improved test gas chamber of this invention.
Figure 3B:
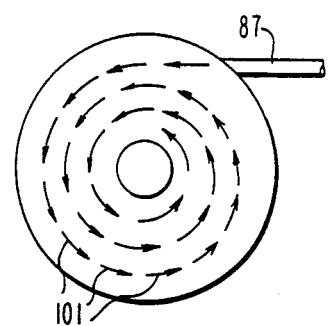
Figure 3C:
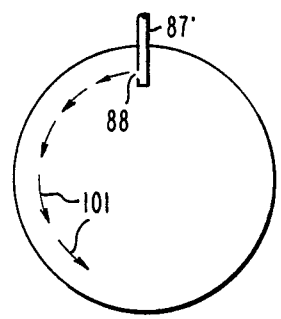

The test gas can be admitted through a tube with a hole located so as to achieve the tangential path direction. This gas flowpath direction can be more clearly appreciated through consideration of FIGS. 3A, 3B and 3C. In FIGS. 3A and 3B, the test gas inlet means 87 is disposed with respect to the chamber 75 as schematically represented to effect the circular gas flow within that chamber. The test gas outlet means 89 can be seen to be disposed at the small end of the cone. The arrows indicated by the reference character 101 demonstrate the circular gas flow of the test gas being used to purge or flood the test gas chamber 75. In FIG. 3C, an alternative test gas inlet means 87' is shown to be disposed so as to be generally perpendicular to the tangential gas flowpath 101. The desired gas flow is achieved by providing a bore 88 in the test gas inlet means 87'.

Figure 4:
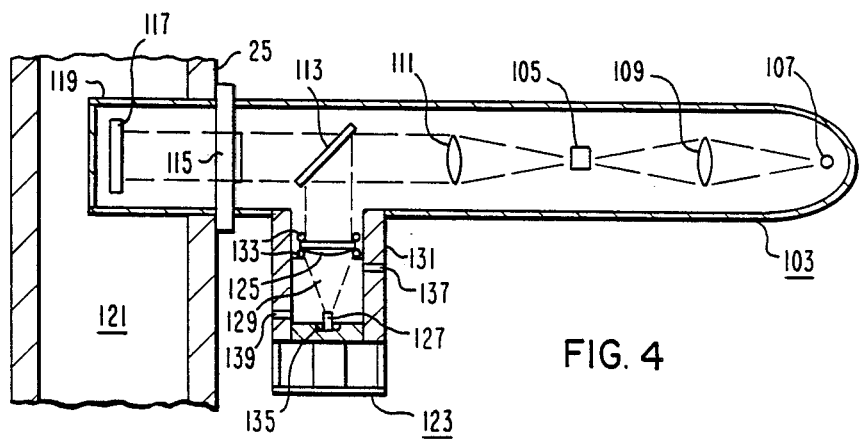
FIG. 4 is a dual beam short path spectrometer incorporating the improved detector assembly of this invention.

Turning now to FIG. 4, an alternative embodiment of a spectrometer which can incorporate the teachings of this invention is schematically illustrated. This alternative embodiment provides a detector assembly in a dual beam short path spectrometer generally indicated by the reference character 103. The short path spectrometer 103 is mounted on one wall of a process conduit such as the gas stack 25 shown in FIG. 1. The spectrometer 103 incorporates the acousto-optic tunable filter described elsewhere herein and indicated at 105. An infrared source 107 is disposed at one side of the AOTF 105. Focusing lens 109 directs the infrared radiation from the source 107 to the AOTF 105. The selected output of the AOTF is directed through a focusing lens 111 and the beam splitter 113. An infrared window 115 separates the source and detector assemblies from the process gas area. A reflector 117 is mounted at the end of a chamber 119 which extends into the process environment 121. The beam splitter 113 allows the infrared radiation which is reflected by reflector means 117 to be directed to the detector assembly 123. The detector assembly 123 is substantially identical to and incorporates the principals described in association with the detector means assembly of FIGS. 2 and 3A, 3B and 3C. This detector assembly includes a focusing lens 125 and an infrared detector means 127 which define the opposed ends of a cone-like chamber 129. The detector assembly 127 and focusing lens 125 are mounted in the detector assembly 123 housing 131 by means of O-rings 133 and 135. Test gas inlet means 137 and test gas outlet means 139 are also provided in the detector assembly housing 131 and operate as described above.

What has been described is an improved test gas chamber for use in spectrometers and the like. The test gas chamber can be used with any number of test gas mixtures without the removal of the device from the process duct location.

What is claimed is:

1. In a broad band automated acousto-optic tunable filter multi-gas infrared analyzer system of the type including:
   (a) means for directing infrared radiation through an environment of interest containing species to be analyzed, which species have predetermined infrared absorption characteristics;
   (b) an acousto-optic tunable filter comprising an optically aligned acousto-optic crystal through which the infrared radiation is passed at a predetermined angle relative to the crystal optic axis, an acoustic transducer means coupled to a variable frequency RF energy source and to the acousto-optic crystal to launch acoustic waves in the crystal to interact with a selected narrow bandwidth portion of the radiation to make it distinguishable from the remaining infrared radiation, which selected narrow bandwidth portion is a function of the frequency of the RF energy and acoustic waves, said selected narrow bandwidth portion being angularly displaced with respect to the non-selected infrared radiation passed through said acoustic-optic tunable filter;
   (c) means for directing the infrared radiation upon said acousto-optic tunable filter;
   (d) infrared radiation detection means which detects the angularly displaced, selected narrow bandwidth portion of the infrared radiation, which detection means generates an output electrical signal as a function of the detected radiation;
   (e) focusing lens means for directing the selected narrow bandwidth portion of the infrared radiation onto said infrared radiation detection means; and
   (f) microcomputer means to which the detection means output electrical signal is applied for determining the species present in a sample cell, and including means for the pulsed operation of the RF energy source to determine the timing and frequency of RF energy applied to the acoustic transducer means mated to the acousto-optic crystal to determine the infrared wavelength selectivity or tuning of the acousto-optic tunable filter, wherein the pulsed operation permits discrimination by said detection means between pulsed emission means of the selected narrow bandwidth portion and emissions from the environment of interest; the improvement to the analyzer system comprising:
   a test gas means including a housing means defining a chamber with a first end having a first aperture, a second end having a second aperture opposite said first aperture, said chamber having a cone-like inner surface tapering from the first aperture to the second aperture, wherein focusing lens means is mounted in said first aperture and said infrared radiation detection means is mounted in said second aperture so as to render an enclosed cone-like chamber, said housing means having a test gas inlet means in communication with said chamber and disposed proximate said first end, said test gas inlet means being so oriented as to introduce test gas into said enclosed cone-like chamber on a tangent to the first end first aperture wherein a tangential flow path direction is achieved within the cone-like chamber, and a test gas outlet means in communication with said chamber and disposed proximate said second end.

2. The analyzer system set forth in claim 1 wherein the microcomputer means includes a microprocessor having memory means for comparing the detected signal to predetermined molecular species indicative signals stored in the memory means, and wherein the memory means provides a predetermined sequence of signals which are applied to the microprocessor to be applied to a frequency synthesizer to vary the frequency of the RF energy applied to the transducer means coupled to the acousto-optic crystal to vary the selection of the narrow bandwidth portion of the infrared radiation which is analyzed, and wherein predetermined frequencies corresponding to predetermined molecular sample species are applied.

3. The analyzer system set forth in claim 1 wherein the RF energy source includes an RF energy frequency synthesizer coupled by electronic signal gate means amplifier which is connected to the acoustic transducer means, and the microcomputer means includes a microprocessor and memory means for applying sequential pulsed control signals to the RF frequency synthesizer to predeterminedly vary the frequency of the RF energy applied to the acousto-optic tunable filter, and wherein control signals are applied to the electronic signal gate means to provide pulse width modulated RF energy to the RF amplifier.

4. The analyzer system set forth in claim 1 wherein the optically aligned acousto-optic crystal is a thallium-arsenic-selenide crystal.

5. The analyzer system set forth in claim 1 wherein the infrared radiation detection means is disposed in relation to the acousto-optic tunable filter such that angular displacement of the selected narrow bandwidth portion is adequate to separate it spatially from the broadband non-selected radiation at the detection means.

* * * * *